(12) United States Patent
Sim et al.

(10) Patent No.: US 10,155,767 B2
(45) Date of Patent: Dec. 18, 2018

(54) THERAPEUTIC AGENT OF ACUTE MYELOID LEUKEMIA CONTAINING 1,3,7-TRISUBSTITUTED 3,4-DIHYDROPYRIMIDO[4,5-D]PYRIMIDINE-2(1H)-ONE DERIVATIVES

(71) Applicant: KOREA INSTITUTE OF SCIENCE AND TECHNOLOGY, Seoul (KR)

(72) Inventors: Tae Bo Sim, Seoul (KR); Han Na Cho, Seoul (KR); Eun Hye Ju, Seoul (KR); Woo Young Hur, Seoul (KR); Ho Jong Yoon, Seoul (KR); Chi Man Song, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/672,987

(22) Filed: Aug. 9, 2017

(65) Prior Publication Data
US 2018/0065969 A1  Mar. 8, 2018

(30) Foreign Application Priority Data

Aug. 9, 2016  (KR) .......................... 10-2016-0101135

(51) Int. Cl.
*C07D 487/04* (2006.01)
(52) U.S. Cl.
CPC .................................. *C07D 487/04* (2013.01)
(58) Field of Classification Search
None
See application file for complete search history.

(56) References Cited

U.S. PATENT DOCUMENTS 7,371,750 B2 * 5/2008 Sim ...................... C07D 471/04
514/234.2

FOREIGN PATENT DOCUMENTS

WO  WO 2005/011597 A2  2/2005

OTHER PUBLICATIONS

Choi et al., "A Type-II Kinase Inhibitor Capable of Inhibiting the T315I "Gatekeeper" Mutant of Bcr-Abl", Journal of Medicinal Chemistry, vol. 53, No. 15, 2010, pp. 5439-5448.
Jain et al., "Phase II Study of the Oral MEK Inhibitor Selumetinib in Advanced Acute Myelogenous Leukemia: A University of Chicago Phase II Consortium Trial", Clinical Cancer Research, vol. 20, No. 2, Jan. 15, 2014, pp. 490-498.
Luo et al., "STK33 kinase inhibitor BRD-8899 has no effect on KRAS-dependent cancer cell viability", PNAS, vol. 109, No. 8, Feb. 21, 2012, pp. 2860-2865.
Nonami et al., "Identification of novel therapeutic targets in acute leukemias with NRAS mutations using a pharmacologic approach", BLOOD, vol. 125, No. 20, May 14, 2015, pp. 3133-3143.

* cited by examiner

*Primary Examiner* — Bong-Sook Baek
(74) *Attorney, Agent, or Firm* — Birch, Stewart, Kolasch & Birch, LLP

(57) ABSTRACT

The present invention provides a therapeutic agent of acute myeloid leukemia containing a 1,3,7-trisubstituted 3,4-dihydropyrimido[4,5-d]pyrimidine-2(1H)-one compound as an active ingredient, which has proliferation inhibitory activity for a human acute myeloid leukemia cell line OCI-AML3 having a NRAS mutant gene while having low inhibitory activity for wild type NRAS and has activity of inhibiting GCK and ACK1 protein kinases at the same time.

3 Claims, No Drawings

THERAPEUTIC AGENT OF ACUTE MYELOID LEUKEMIA CONTAINING 1,3,7-TRISUBSTITUTED 3,4-DIHYDROPYRIMIDO[4,5-D]PYRIMIDINE-2(1H)-ONE DERIVATIVES

CROSS-REFERENCE TO RELATED APPLICATION

This non-provisional application claims the benefit under 35 U.S.C. § 119(a) to Patent Application No. 10-2016-0101135, filed in the Republic of Korea on Aug. 9, 2016, all of which are hereby expressly incorporated by reference into the present application.

BACKGROUND

(a) Technical Field

The present disclosure relates to a therapeutic agent of acute myeloid leukemia including 1,3,7-trisubstituted 3,4-dihydropyrimido[4,5-d]pyrimidine-2(1H)-one derivatives, which has proliferation inhibitory activity for a human acute myeloid leukemia cell line OCI-AML3 having a NRAS mutant gene while having low inhibitory activity for a wild-type NRAS and has activity of inhibiting GCK and ACK1 protein kinases at the same time.

(b) Background Art

Acute myeloid leukemia (AML) is a kind of blood cancer which is caused by abnormal growth or differentiation of myeloid leukocyte progenitor cells and considered the most common acute leukemia (65%) in adults. 16% or more of AML patients have a point-mutated RAS (small G protein) protein and NRAS mutations account for the majority (10% or more) of RAS kinases. For this reason, the NRAS G protein has been considered as a promising drug target for treating AML. When the RAS as a protooncogene is mutated, the RAS is continuously activated (gain-of-function) and various signaling systems of the RAS downstream are activated to accelerate the growth of cancer cells.

Over the last 40 years, RAS point mutants or key signaling molecules of the RAS downstream are proposed as targets, but due to the complexity and compensating effects of the mutated RAS signaling system, in vivo experiments and clinical trials are not extended. For example, selumetinib (AZD 6244), which inhibits MEK, a key molecule of the RAS downstream, does not have a treatment effect in all three AML patients with the NRAS mutant gene in a clinical 2 phase. In addition, as an attempt for finding targets, proteins TBK1, STK33 and GATA2 having a genetically synthetic lethal relation with KRAS mutation have been found through RNA interference (RNAi) screening. However, this attempt also did not result in clinical treatment effects. In particular, in the case of STK33, it has been proved that a therapeutic strategy using KRAS mutation and synthetic lethal principles may not be established through cell-based pharmacologic screening at a pre-clinical stage. Recently, irreversible inhibitors and allosteric inhibitors for KRAS G12C point mutations have been studied, but the studies are still in early stages. Further, recently, a compound GNF 7 that selectively inhibits a RAS mutation signaling system has been ensured and an inhibitory effect in preclinical leukemia models has been confirmed through cell-based pharmacological screening. An action mechanism of the compound GNF 7 is to inhibit two kinases GCK and ACK1 at the same time which specifically contribute to cell growth in the RAS mutation downstream. This indicates the efficacy even in an actual AML patient cell sample having the NRAS mutation.

Meanwhile, in International Patent Publication No. WO 2005-011597 (Patent Document 1), there is disclosed a compound having 3,4-dihydropyrimido [4,5-d] pyrimidin-2(1H)-one as a scaffold and it is disclosed that the compound is effective for the treatment of diseases or symptoms caused by activity of kinase such as Abl and BCR-Abl. However, in Patent Document 1, it is disclosed that the compound is useful as a therapeutic agent of chronic myelogenous leukemia (CML) based on BCR-Abl inhibitory activity.

The above information disclosed in this Background section is only for enhancement of understanding of the background of the invention and therefore it may contain information that does not form the prior art that is already known in this country to a person of ordinary skill in the art.

PRIOR ART

Patent Document (Patent Document 1) International Patent Publication No. WO 2005-011597

Non-Patent Document (Non-Patent Document 1) Choi H G, Ren P, Adrian F, et al. A type-II kinase inhibitor capable of inhibiting the T315I "gatekeeper" mutant of Bcr-Abl. J Med Chem. 2010; 53 (15): 5439-5448.

(Non-Patent Document 2) Luo T, Masson K, Jaffe J D, et al. STK33 kinaseinhibitor BRD-8899 has no effect on KRASdependentcancer cell viability. Proc Natl AcadSci USA. 2012; 109(8): 2860-2865.

(Non-Patent Document 3) Jain N, Curran E, Iyengar N M, et al. Phase IIstudy of the oral MEK inhibitor selumetinib inadvanced acute myelogenous leukemia:a University of Chicago phase II consortium trial. Clin Cancer Res. 2014; 20(2): 490-498.

SUMMARY OF THE DISCLOSURE

The present invention has been made in an effort to solve the above-described problems associated with prior art.

The present inventors have continuously conducted researches to develop effective compounds for target-treatment, prevention and alleviation of acute myeloid leukemia (AML) which is fatal in tumor diseases. As a result, the present inventors have selected a compound having low inhibitory activity for wild type-NRAS while having excellent inhibitory activity for NRAS mutants by simultaneously inhibiting two kinases of GCK and ACK1 associated with NRAS which is one of genes causing AML and completed the present invention.

Therefore, the present invention has been made in an effort to provide a therapeutic agent of acute myeloid leukemia (AML) including a 1,3,7-trisubstituted 3,4-dihydropyrimido[4,5-d]pyrimidine-2(1H)-one compound as an active ingredient, which has proliferation inhibitory activity for a human acute myeloid leukemia cell line OCI-AML3 having a NRAS mutant gene while having low inhibitory activity for wild type-NRAS and has activity of inhibiting GCK and ACM protein kinases at the same time.

In one aspect, the present invention provides a therapeutic agent of acute myeloid leukemia having a selective NRAS inhibition mechanism, in which a 1,3,7-trisubstituted 3,4-dihydropyrimido[4,5-d]pyrimidine-2(1H)-one compound represented by the following Chemical Formula 1 or a pharmaceutically acceptable salt is included as an active ingredient.

[Chemical Formula 1]

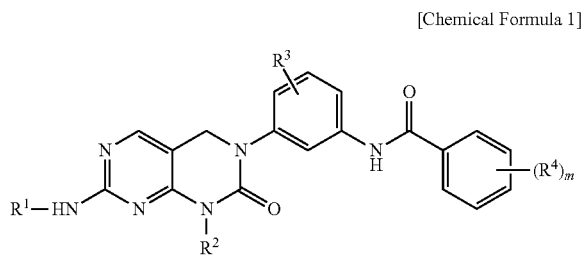

In Chemical Formula 1, $R^1$ represents a pyridine group substituted with a substituent selected from piperazinyl or N—($C_1$-$C_6$ alkyl) piperazinyl, $R^2$ represents a hydrogen atom or a $C_1$-$C_6$ alkyl group, $R^3$ represents a $C_1$-$C_6$ alkyl group, $R^4$ represents a $C_1$-$C_6$ haloalkyl group substituted with 1 to 10 halogen atoms, and M represents an integer of 1 to 2 as the number of $R^4$ substituents.

The pharmaceutical composition of the present invention has proliferation inhibitory activity for a human acute myeloid leukemia cell line OCI-AML3 having a NRAS mutant gene while having low inhibitory activity for wild type-NRAS. Further, the pharmaceutical composition of the present invention has activity of inhibiting GCK and ACK1 protein kinases at the same time. Therefore, the pharmaceutical composition of the present invention has an excellent effect on target treatment, prevention and alleviation of acute myeloid leukemia.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to a pharmaceutical composition for target treatment, prevention and alleviation of acute myeloid leukemia, in which a 1,3,7-trisubstituted 3,4-dihydropyrimido[4,5-d]pyrimidine-2(1H)-one compound represented by the following Chemical Formula 1 or a pharmaceutically acceptable salt is included as an active ingredient.

[Chemical Formula 1]

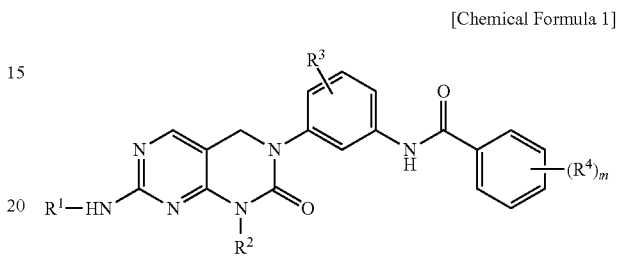

In Chemical Formula 1, $R^1$ represents a pyridine group substituted with a substituent selected from piperazinyl or N—($C_1$-$C_6$ alkyl) piperazinyl, $R^2$ represents a hydrogen atom or a $C_1$-$C_6$ alkyl group, $R^3$ represents a $C_1$-$C_6$ alkyl group, $R^4$ represents a $C_1$-$C_6$ haloalkyl group substituted with 1 to 10 halogen atoms, and M represents an integer of 1 to 2 as the number of $R^4$ substituents.

The compound which may be included as the active ingredient in the pharmaceutical composition of the present invention may be represented by the following Chemical Formula 1a as a detailed example.

[Chemical Formula 1a]

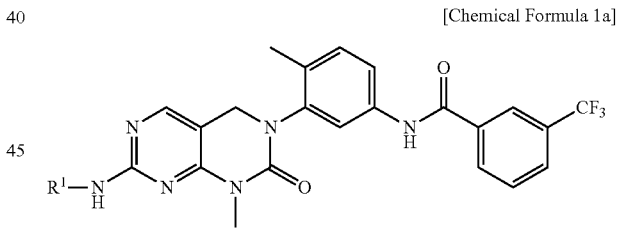

(In Chemical Formula 1a, $R^1$ is the same as defined in Chemical Formula 1 above.)

The compound represented by Chemical Formula 1 which may be included as the active ingredient in the pharmaceutical composition of the present invention may be more preferably:

N-(3-(7-((6-(4-methylpiperazin-1-yl)pyridin-3-yl)amino)-1-methyl-2-oxo-1,4-dihydropyrimido[4,5-d]pyrimidin-3-(2H)-yl)-4-methylphenyl)-3-(trifluoromethyl)benzamide; and N-(3-(7-((6-(4-ethylpiperazin-1-yl)pyridin-3-yl)amino)-1-methyl-2-oxo-1,4-dihydropyrimido[4,5-d]pyrimidin-3-(2H)-yl)-4-methylphenyl)-3-(trifluoromethyl)benzamide; or a pharmaceutically acceptable salt thereof.

The compound represented by Chemical Formula 1 included in the pharmaceutical composition of the present invention may be included as a form of a pharmaceutically acceptable salt. The pharmaceutically acceptable salt may be prepared and used by a typical method known in the art. For example, the pharmaceutically acceptable acidic salt thereof may be formed together with non-toxic inorganic acid such as hydrochloric acid, bromic acid, sulfonic acid, amidosulfuric acid, phosphoric acid, and nitric acid, or non-toxic organic acid such as propionic acid, succinic acid, glycolic acid, stearic acid, lactic acid, tartaric acid, citric acid, paratoluenesulfonic acid, and methanesulfonic acid.

According to the present invention, the compound represented by Chemical Formula 1 has excellent proliferation inhibitory activity for a NRAS mutant cell line which is one of cause genes of acute myeloid leukemia (AML). Further, the compound represented by Chemical Formula 1 does not exhibit inhibitory activity for a wild type-NRAS AML cell line. Further, the compound represented by Chemical Formula 1 has excellent inhibitory activity for GCK and ACK1 kinases at the same time.

Accordingly, the pharmaceutical composition including the compound represented by Chemical Formula 1, a pharmaceutically acceptable salt thereof, a solvate thereof, or a hydrate thereof as an active ingredient is excellent as a therapeutic agent for AML caused by the NRAS mutant cell line.

The pharmaceutical composition of the present invention includes the compound represented by Chemical Formula 1, a pharmaceutically acceptable salt thereof, a solvate thereof, or a hydrate thereof as an active ingredient. In addition, the pharmaceutical composition may be prepared as typical formulations in a pharmaceutical field, for example, formulations for oral administration such as tablets, capsules, troches, liquids and suspensions or formulations for parenteral administration by adding typical non-toxic pharmaceutically acceptable carriers, adjuvants, excipients, and the like thereto.

As the excipients may be used in the pharmaceutical composition of the present invention, sweeteners, binders, dissolvents, solubilizing agents, wetting agents, emulsifiers, isotonic agents, adsorbents, disintegrants, antioxidants, preservatives, lubricants, fillers, fragrances, and the like. For example, the excipients may include lactose, dextrose, sucrose, mannitol, sorbitol, cellulose, glycine, silica, talc, stearic acid, stearin, magnesium stearate, magnesium aluminum silicate, starch, gelatin, tragacanth gum, arginic acid, sodium alginate, methylcellulose, sodium carboxylmethylcellulose, agar, water, ethanol, polyethylene glycol, polyvinylpyrrolidone, sodium chloride, calcium chloride, orange essence, strawberry essence, vanilla flavor, and the like.

A dose of the compound according to the present invention administered to the human body may vary depending on age, body weight, gender, dosage form, health condition and disease severity of a patient. In addition, the dose may be generally 0.01 to 1,000 mg/day based on an adult patient having a body weight of 70 kg and the compound may also be administered once to several times a day at regular time intervals according to the judgment of a doctor or pharmacist.

Meanwhile, a method for preparing the compound represented by Chemical Formula 1 is described in detail in International Patent Publication No. WO 2005-011597.

The following Reaction Formula 1 illustrates one embodiment of a representative method of preparing the compound represented by Chemical Formula 1.

The following Reaction Formula 1 illustrates one embodiment of a representative method of preparing the compound represented by Chemical Formula 1. The following Reaction Formula 1 includes i) a process of preparing a compound represented by the following Chemical Formula 4 by amidation-binding an amide compound represented by the following Chemical Formula 2 and an acid chloride compound represented by the following Chemical Formula 3; and ii) a process of preparing a 1,3,7-trisubstituted 3,4-dihydropyrimido[4,5-d]pyrimidine-2(1H)-one compound represented by Chemical Formula 1 of the present invention by Buckwald-aminating a compound represented by the following Chemical Formula 4 and an amine compound represented by the following Chemical Formula 5.

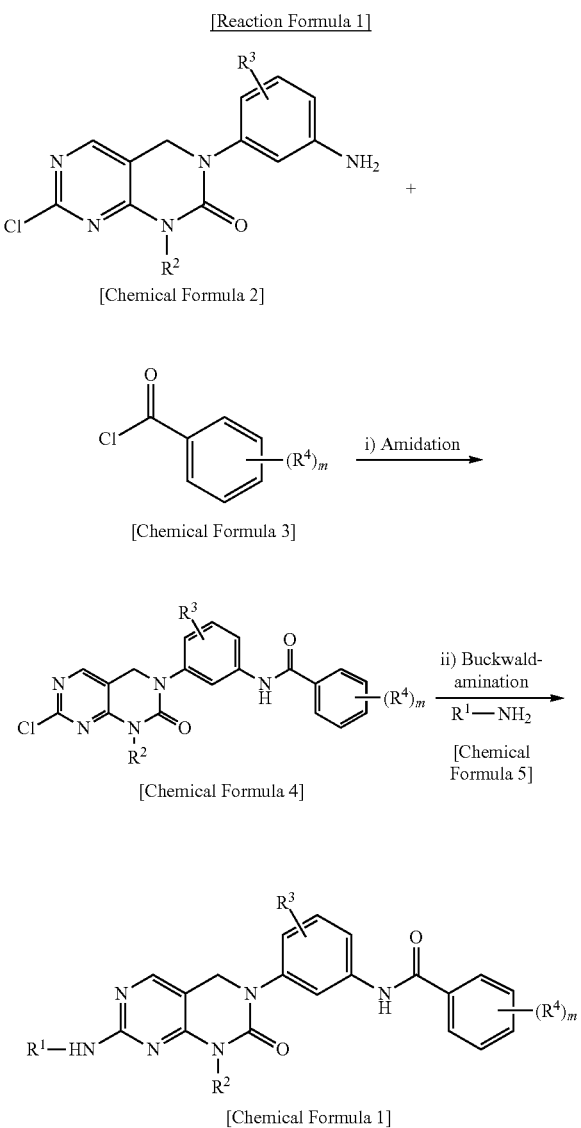

(In Reaction Formula 1, $X_1$, $X_2$, $R_1$, $R_2$ and n are the same as described above, respectively.)

The i) amidation-binding performed in the preparing method according to Reaction Formula 1 above may be performed in the presence of a base such as carbonate, sulfate, phosphate and alkoxide of an alkali metal or an alkaline earth metal. Particularly, the base may use $K_2CO_3$, $CsCO_3$, $Na_2CO_3$, $K_3PO_4$, NaOt-Bu, KOt-Bu, and the like. A reaction solvent may use a typical organic solvent including tetrahydrofuran, dichloromethane, dioxane, N,N-dimethylformamide, N,N-dimethylsulfoxide, 2-butanol, 2-pentanol, and the like. A reaction temperature is in a range of 10° C. to 50° C., and preferably, maintains a temperature range around room temperature of 20° C. to 30° C.

In the ii) Buckwald-amination performed in the preparing method according to Reaction Formula 1 above, a metal compound may use $Pd_2(dba)_3$, $Pd(OAc)_2$, $PdCl_2(PPh_3)_2$, $Pd(PPh_3)_4$, and the like. A ligand may use Xantphos (Cas number: 161265-03-8), Davephos (Cas number: 213697-53-1), Johnphos (Cas number: 224311-51-7), X-phos (Cas number: 564483-18-7), tert-Butyl Xphos (Cas 564483-19-8), and the like. In addition, the base may use carbonate, sulfate, phosphate, alkoxide, and the like of an alkali metal or an alkaline earth metal, and particularly $K_2CO_3$, $CsCO_3$, $Na_2CO_3$, $K_3PO_4$, NaOt-Bu, KOt-Bu, and the like. A reaction solvent may use a typical organic solvent including tetrahydrofuran, dioxane, N,N-dimethylformamide, N,N-dimethylsulfoxide, 2-butanol, 2-pentanol, and the like. The reaction temperature is in a range of 50° C. to 200° C., and preferably, maintains a range of 80° C. to 150° C.

EXAMPLES

The following examples illustrate the invention and are not intended to limit the same.

Representative Synthesis Example

Synthesis Example exemplifies a representative synthesis method of a compound used in an experiment of measuring proliferation inhibitory activity and kinase inhibitory activity of the following NRAS cell line.

Step 1

N-(3-(7-chloro-1-methyl-2-oxo-1,4-dihydropyrimido[4,5-d]pyrimidin-3(2H)-yl)-4-methylphenyl)-3-(trifluoromethyl)benzamide

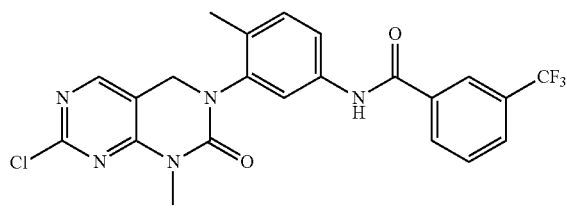 [SMILES: Cc1ccc(NC(=O)c2cccc(C(F)(F)F)c2)cc1N1Cc2cnc(Cl)nc2N(C)C1=O]

3-(5-amino-2-methylphenyl)-7-chloro-1-methyl-3,4-dihydropyrimido[4,5-d]pyrimidine-2(1H)-one (230 g, 0.76 mmol) was dissolved in dichloromethane (2.52 mL), added with 3-(trifluoromethyl)benzoyl chloride (0.12 mL, 0.84 mmol) and potassium carbonate (209.3 mg, 1.51 mmol), and then stirred at room temperature. After 1 hour, when the reaction was completed, an organic layer was extracted and collected using dichloromethane and water, and dried and concentrated with anhydrous magnesium sulfate. The residue was purified by column chromatography to obtain a desired compound (262.1 mg, 72.8%) as a white solid.

$^1$H NMR (400 MHz, DMSO-$d_6$) δ 8.40 (s, 1H), 8.11 (m, 2H), 8.07 (d, J=7.6 Hz, 1H), 7.80 (d, J=2 Hz, 1H), 7.78 (s, 1H), 7.62 (t, J=7.6 Hz, 1H), 7.16 (d, J=8.4 Hz, 1H), 4.78 (d, J=15.6 Hz, 1H), 4.54 (d, J=15.6 Hz, 1H), 3.50 (s, 3H), 1.91 (s, 3H).

Step 2

N-(4-methyl-3-(1-methyl-7-((1-methyl-1H-pyrazol-4-yl)amino)-2-oxo-1,4-dihydropyrimido[4,5-d]pyrimidin-3(2H)-yl)phenyl)-3-(trifluoromethyl)benzamide

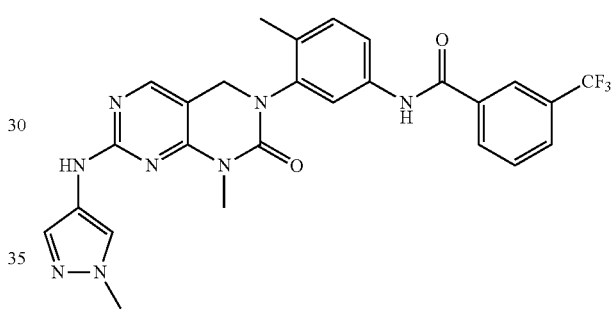

N-(3-(7-chloro-1-methyl-2-oxo-1,4-dihydropyrimido[4,5-d]pyrimidin-3(2H)-yl)-4-methylphenyl)-3-(trifluoromethyl)benzamide (50 mg, 0.11 mmol) was dissolved in 2-butanol (0.55 mL). 1-methyl-IH-pyrazol-4-amine (11.8 mg, 0.12 mmol) and potassium carbonate (76 mg, 0.55 mmol) were added in a reaction container, the reaction container was transferred to an oil bath heated to 110° C., $Pd_2(dba)_3$ (20.1 mg, 0.02 mmol) and Xphos (10.5 mg, 0.02 mmol) were added and then stirred for 90 minutes. When the reaction was completed, the reaction mixture was filtered and concentrated using a celite pad. The residue was purified by MPLC to obtain the desired compound (20 mg, 14.3%) as a white solid.

$^1$H NMR (400 MHz, DMSO-$d_6$) δ 10.51 (s, 1H), 9.40 (s, 1H), 8.29 (s, 1H), 8.25 (d, J=8.4 Hz, 1H), 8.08 (s. 1H), 7.96 (d, J=7.6 Hz, 1H), 7.79 (m, 3H), 7.63 (dd, J=2 Hz, J=8 Hz, 1H), 7.50 (s, 1H), 7.30 (d, J=8.4 Hz, 1H), 4.66 (d, J=14 Hz, 1H), 4.48 (d, J=14 Hz, 1H), 3.80 (s, 3H), 3.34 (s, 3H), 2.12 (s, 3H).

The following compounds may be obtained by using proper starting materials in the method described in Representative Synthesis Example above.

Compound 1

N-(3-(7-((6-(4-ethylpiperazin-1-yl)pyridin-3-yl)amino)-1-methyl-2-oxo-1,4-dihydropyrimido[4,5-d]pyrimidin-3-(2H)-yl)-4-methylphenyl)-3-(trifluoromethyl)benzamide

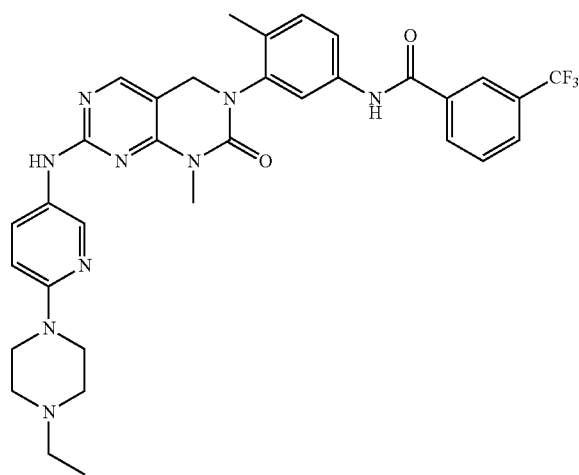 [SMILES: CCN1CCN(c2ccc(Nc3ncc4c(n3)N(C)C(=O)N(c3cc(NC(=O)c5cccc(C(F)(F)F)c5)ccc3C)C4)cn2)CC1]

$^1$H NMR (400 MHz, DMSO-d$_6$) δ 10.53 (s, 1H), 9.32 (s, 1H), 8.46 (d, J=2.4 Hz, 1H), 8.30 (s, 1H), 8.26 (d, J=8 Hz, 1H), 8.09 (s, 1H), 7.97 (d, J=7.6 Hz, 1H), 7.88 (dd, J=2.4 Hz, J=8 Hz, 1H), 7.89 (m, 2H), 7.64 (dd, J=2 Hz, J=8 Hz, 1H), 7.31 (d, J=8.8H, 1H), 6.82 (d, J=9.2 Hz, 1H), 4.68 (d, J=14, 1H), 4.50 (d, J=14, 1H), 3.39 (s, 4H), 3.33 (s, 3H), 2.45 (s, 4H), 2.35 (q, J=7.2 Hz, 2H), 2.13 (s, 3H), 1.03 (t, J=6.8 Hz, 3H).

Compound 2

N-(3-(7-((3-(4-ethylpiperazin-1-yl)phenyl)amino)-1-methyl-2-oxo-1,4-dihydropyrimido[4,5-d]pyrimidin-3-(2H)-yl)-4-methylphenyl)-3-(trifluoromethyl)benzamide

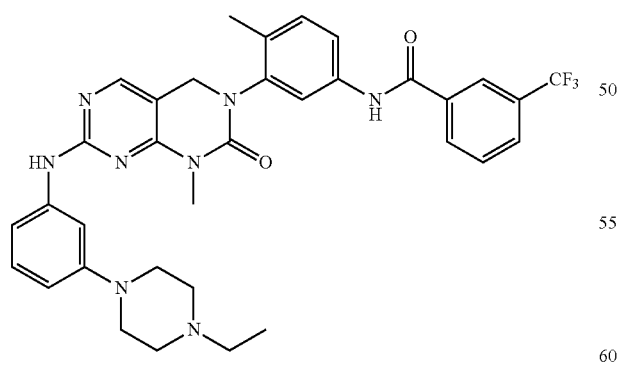

$^1$H NMR (400 MHz, DMSO-d$_6$) δ 9.96 (s, 1H), 8.57 (s, 1H), 8.34 (m, 2H), 8.16 (s, 1H), 7.96 (d, J=7.6 Hz, 1H), 7.92 (d, J=2 Hz, 1H), 7.81 (t, J=7.6 Hz, 1H), 7.71 (dd, J=2.4 Hz, J=8 Hz, 1H), 7.63 (t, J=2 Hz, 1H), 7.32 (d, J=8.4 Hz, 1H), 7.28 (d, 1.2 Hz, 1H), 7.19 (t, J=8 Hz, 1H), 6.64 (dd, J=1.6 Hz, J=8 Hz, 1H), 4.82 (d, J=14 Hz, 1H), 4.61 (d, J=14 Hz, 1H), 3.45 (s, 3H), 3.25 (t, J=3.25, J=4.8 Hz, 4H), 2.60 (t, J=4.8 Hz, 4H), 2.44 (q, J=7.2 Hz, 2H), 2.22 (s, 3H), 1.11 (t, J=7.2 Hz, 3H).

Compound 3

N-(4-methyl-3-(1-methyl-7-((1-methyl-1H-pyrazol-4-yl)amino)-2-oxo-1,4-dihydropyrimido[4,5-d]pyrimidin-3(2-yl)phenyl)-3-(trifluoromethyl)benzamide

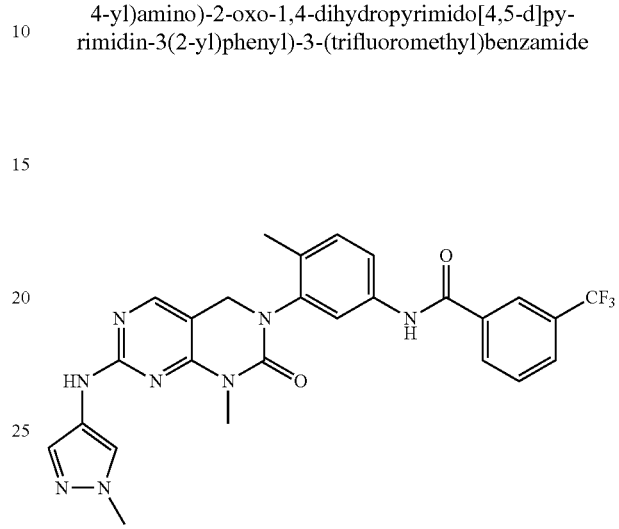

$^1$H NMR (400 MHz, DMSO-d$_6$) δ 10.51 (s, 1H), 9.40 (s, 1H), 8.29 (s, 1H), 8.25 (d, J=8.4 Hz, 1H), 8.08 (s. 1H), 7.96 (d, J=7.6 Hz, 1H), 7.79 (m, 3H), 7.63 (dd, J=2 Hz, J=8 Hz, 1H), 7.50 (s, 1H), 7.30 (d, J=8.4 Hz, 1H), 4.66 (d, J=14 Hz, 1H), 4.48 (d, J=14 Hz, 1H), 3.80 (s, 3H), 3.34 (s, 3H), 2.12 (s, 3H).

Compound 4

N-(4-methyl-3-(1-methyl-2-oxo-7-(phenylamino)-1,4-dihydropyrimido[4,5-d]pyrimidin-3(2H)-yl)phenyl)-3-(trifluoromethyl)benzamide

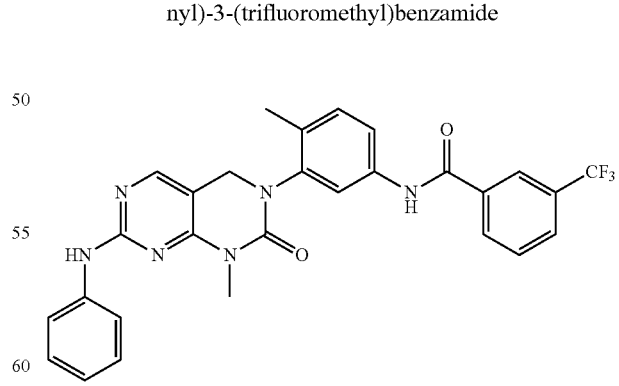

$^1$H NMR (400 MHz, DMSO-d$_6$) δ 10.52 (s, 1H), 9.56 (s, 1H), 8.30 (s, 1H), 8.26 (d, J=7.6 Hz, 1H), 8.15 (s, 1H), 7.78 (m, 4H), 7.64 (dd, J=2 Hz, J=8 Hz, 1H), 7.29 (q, J=8 Hz, 3H), 6.93 (t, J=7.8, 1H), 4.70 (d, J=14.4 Hz, 1H), 4.52 (d, J=14.4 Hz, 1H), 3.33 (s, 3H), 2.13 (s, 3H).

Compound 5

N-(3-(7-(cyclohexylamino)-1-methyl-2-oxo-1,4-dihydropyrimido[4,5-d]pyrimidin-3(2H)-yl)-4-methylphenyl)-3-(trifluoromethyl)benzamide

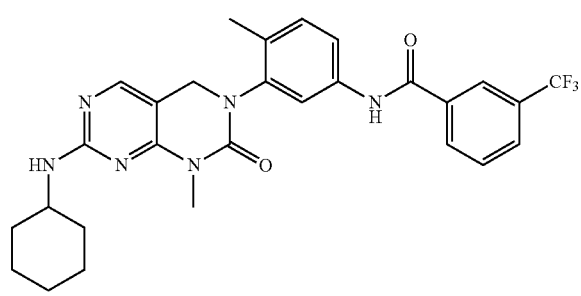 [SMILES: Cc1ccc(NC(=O)c2cccc(C(F)(F)F)c2)cc1N1Cc2cnc(NC3CCCCC3)nc2N(C)C1=O]

$^1$H NMR (400 MHz, DMSO-$d_6$) δ 10.51 (s, 1H), 8.30 (s, 1H), 8.26 (d, J=8 Hz, 1H), 7.96 (d, J=11.2 Hz, 2H), 7.78 (m, 2H), 7.64 (dd, J=2 Hz, 1=8 Hz, 1H), 7.30 (d, J=8.4 Hz, 1H), 6.95 (s, 1H), 4.60 (d, J=14 Hz, 1H), 4.41 (d, J=14 Hz, 1H), 3.70 (t, J=4.4 Hz, 1H), 3.26 (s, 3H), 2.12 (s, 3H), 1.90 (s, 2H), 1.71 (s, 2H), 1.59 (d, J=12 Hz, 1H), 1.25 (m, 4H), 1.11 (t, J=11.2 Hz, 1H).

Compound 6

N-(3-(7-((2-hydroxyethyl)amino)-1-methyl-2-oxo-1,4-dihydropyrimido[4,5-d]pyrimidin-3(2H)-yl)-4-methylphenyl)-3-(trifluoromethyl)benzamide

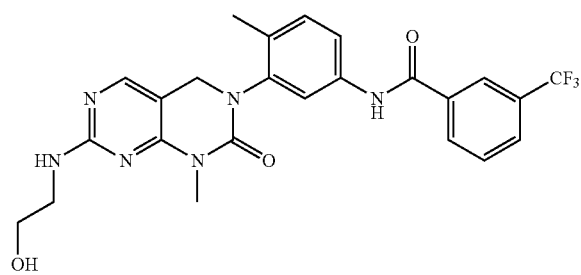 [SMILES: Cc1ccc(NC(=O)c2cccc(C(F)(F)F)c2)cc1N1Cc2cnc(NCCO)nc2N(C)C1=O]

$^1$H NMR (400 MHz, DMSO-$d_6$) δ 8.30 (s, 1H), 8.26 (d, J=7.6 Hz, 1H), 7.97 (s, 1H), 7.96 (s, 1H), 7.77 (m, 2H), 7.63 (dd, J=2 Hz, J=8 Hz, 1H), 7.30 (d, J=8.4 Hz, 1H), 6.96 (t, J=5.6 Hz, 1H), 4.66 (t, J=5.6 Hz, 1H), 4.61 (d, J=14 Hz, 1H), 4.42 (d, J=14 Hz, 1H), 3.53 (q, J=6 Hz, 2H), 3.37 (q, J=5.6 Hz, 2H), 3.33 (s, 3H), 2.11 (s, 3H).

Compound 7

N-(3-(7-(cyclopropylamino)-1-methyl-2-oxo-1,4-dihydropyrimido[4,5-d]pyrimidin-3(2H)-yl)-4-methylphenyl)-3-(trifluoromethyl)benzamide

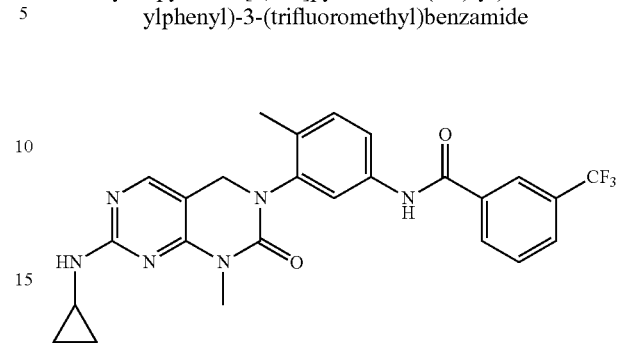

$^1$H NMR (400 MHz, DMSO-$d_6$) δ 10.51 (s, 1H), 8.31 (s, 1H), 8.27 (d, J=8 Hz, 1H), 7.99 (s, 1H), 7.97 (d, J=8 Hz, 1H), 7.79 (m, 2H), 7.64 (dd, J=2 Hz, J=8 Hz, 1H), 7.30 (m, 2H), 4.63 (d, J=13.6 Hz, 1H), 4.43 (d, J=14 Hz, 1H), 3.28 (s, 3H), 2.72 (m, 1H), 2.12 (s, 3H), 0.66 (m, 2H), 0.48 (m, 2H).

The compounds synthesized above were compared with each other by measuring proliferation inhibitory activity of a NARS mutagenesis cell line and inhibitory activity of GCK and ACK1 kinases by the following methods.

TEST EXAMPLES

Test Example 1. Proliferation Inhibitory Activity

With respect to each of the compounds synthesized in Synthesis Examples, $GI_{50}$ values were calculated by measuring proliferation inhibitory abilities for mt-NRAS (G12D) Ba/F3, U937 (wt-NRAS), and OCI-AML3 (mt-NRAS) cell lines. The calculated $GI_{50}$ values were listed in the following Table 1.

TABLE 1

| | | Proliferation inhibitory ability ($GI_{50}$, μM) | | |
|---|---|---|---|---|
| Test compound | $R^1$ substituent | OCI-AML3 (N-RasQ61L) | U937 (N-Ras WT) | Ba/F3 (N-Ras G12D) |
| Compound 1 | 6-(4-ethylpiperazin-1-yl)pyridin-3-yl | A | D | A |
| Compound 2 | 3-(4-ethylpiperazin-1-yl)phenyl | A | A | A |
| Compound 3 | 1-methyl-1H-pyrazole-4-yl | B | C | A |
| Compound 4 | Phenyl | B | E | B |
| Compound 5 | Cyclohexyl | E | E | B |
| Compound 6 | 2-hydroxyethyl | C | E | E |
| Compound 7 | Cyclopropyl | B | E | B |

[Classification of $GI_{50}$]
A: Less than 0.2 μM,
B: 0.2 to 0.7 μM,
C: 0.7 μM to 1.2 μM,
D: 1.2 to 2.0 μM,
E: 2.0 μM or more According to the results in Table 1 above, the compounds 1 to 7 are compounds having, mother nucleus, 3,4-dihydropyrimido[4,5-d]pyrimidin-2(1H)-one, but there is a difference in the seventh substituent ($R^1$) of the scaffold. That is, the compound represented by Chemical Formula 1 has a remarkable difference in the proliferation inhibitory activity against the NRAS cell line depending on the substituent $R^1$. According to the results of Table 1 above, it can be seen that when the substituent $R^1$ is a 'piperazinyl-substituted pyridine group', the compound has the proliferation inhibitory activity for the human acute myeloid leukemia cell line OCI-AML3 having a NRAS mutant gene while having low inhibitory activity for wild type-NRAS (U937) and the effect thereof is remarkable.

Test Example 2. Kinase Inhibitory Activity

With respect to the compounds of the present invention, $IC_{50}$ values were calculated by measuring inhibitory ability for two kinases of GCK and ACK1. The calculated $IC_{50}$ values were listed in the following Table 2.

TABLE 2

| Test compound | $R^1$ substituent | GCK | ACK1 |
| --- | --- | --- | --- |
| Compound 1 | 6-(4-ethylpiperazin-1-yl)pyridin-3-yl | A | A |
| Compound 2 | 3-(4-ethylpiperazin-1-yl)phenyl | A | C |
| Compound 3 | 1-methyl-1H-pyrazole-4-yl | A | A |
| Compound 4 | Phenyl | C | B |
| Compound 5 | Cyclohexyl | E | C |
| Compound 6 | 2-hydroxyethyl | B | A |
| Compound 7 | Cyclopropyl | B | B |

[Classification of $GI_{50}$]
A: Less than 0.03 μM,
B: 0.03 to 0.045 μM,
C: 0.045 μM to 0.1 μM,
D: 0.1 to 0.3 μM,
E: 0.3 μM or more The compound represented by Chemical Formula 1 has a remarkable difference in inhibitory activity for protein kinases GCK and ACK1 according to a substituent $R^1$. According to the results of Table 2 above, it can be seen that when the substituent $R^1$ is a 'piperazinyl-substituted pyridine group' or 'methyl-substituted pyrazole group', the compound has inhibitory activity for the kinases GCK and ACK1 at the same time.

PREPARATION EXAMPLES

Meanwhile, a novel compound represented by Chemical Formula 1 according to the present invention can be formulated into various forms according to the purpose. Next, some formulation methods of including the compound represented by Chemical Formula 1 as an active ingredient according to the present invention will be exemplified, but the present invention is not limited thereto.

Preparation Example 1: Tablets (Direct Pressurization)

After 5.0 mg of an active ingredient was sieved, 14.1 mg of lactose, 0.8 mg of crospovidone USNF and 0.1 mg of magnesium stearate were mixed and pressurized to prepare tablets.

Preparation Example 2: Tablets (Wet Assembly)

After 5.0 mg of an active ingredient was sieved, 16.0 mg of lactose and 4.0 mg of starch were mixed. 0.3 mg of polysorbate 80 was dissolved in pure water, and then an appropriate amount of the solution was added and atomized. After drying, particles were sieved and then mixed with 2.7 mg of colloidal silicon dioxide and 2.0 mg of magnesium stearate. The particles were pressurized to prepare tablets.

Preparation Example 3: Powder and Capsules

After 5.0 mg of an active ingredient was sieved, 14.8 mg of lactose, 10.0 mg of polyvinylpyrrolidone, and 0.2 mg of magnesium stearate were mixed. The mixture was filled in hard No. 5 gelatin capsules using an appropriate apparatus.

Preparation Example 4: Injections

Injections were prepared by including 100 mg of an active ingredient and further including 180 mg of mannitol, 26 mg of $Na_2HPO_4 \cdot 12H_2O$ and 2974 mg of distilled water.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A pharmaceutical composition for treatment or alleviation of acute myeloid leukemia caused by a NRAS mutant cell line, wherein the pharmaceutical composition comprises a compound selected from the group consisting of N-(3-(7-((6-(4-methylpiperazin-1-yl)pyridin-3-yl)amino)-1-methyl-2-oxo-1,4-dihydropyrimido[4,5-d]pyrimidin-3-(2H)-yl)-4-methylphenyl)-3-(trifluoromethyl)benzamide and N-(3-(7-((6-(4-ethylpiperazin-1-yl)pyridin-3-yl)amino)-1-methyl-2-oxo-1,4-dihydropyrimido[4,5-d]pyrimidin-3-(2H)-yl)-4-methylphenyl)-3-(trifluoromethyl)benzamide, or a pharmaceutically acceptable salt thereof.

2. The pharmaceutical composition of claim 1, wherein the compound is selected from the group consisting of N-(3-(7-((6-(4-methylpiperazin-1-yl)pyridin-3-yl)amino)-1-methyl-2-oxo-1,4-dihydropyrimido [4,5-d]pyrimidin-3-(2H)-yl)-4-methylphenyl)-3-(trifluoromethyl)benzamide and a pharmaceutically acceptable salt thereof.

3. The pharmaceutical composition of claim 1, wherein the compound is selected from the group consisting of N-(3-(7-((6-(4-ethylpiperazin-1-yl)pyridin-3-yl)amino)-1-methyl-2-oxo-1,4-dihydropyrimido [4,5-d]pyrimidin-3-(2H)-yl)-4-methylphenyl)-3-(trifluoromethyl)benzamide and a pharmaceutically acceptable salt thereof.

* * * * *